(12) United States Patent
Krill et al.

(10) Patent No.: US 10,479,754 B2
(45) Date of Patent: Nov. 19, 2019

(54) SYNTHESIS OF METHACRYLIC ACID FROM METHACROLEIN-BASED ALKYL METHACRYLATE

(71) Applicant: Roehm GmbH, Darmstadt (DE)

(72) Inventors: Steffen Krill, Muehltal (DE); Matthias Groemping, Darmstadt (DE); Alexander Lygin, Griesheim (DE)

(73) Assignee: Roehm GmbH, Darmstadt (DE)

(*) Notice: Subject to any disclaimer, the term of this patent is extended or adjusted under 35 U.S.C. 154(b) by 0 days.

(21) Appl. No.: 15/753,206

(22) PCT Filed: Sep. 9, 2016

(86) PCT No.: PCT/EP2016/071241
§ 371 (c)(1),
(2) Date: Feb. 16, 2018

(87) PCT Pub. No.: WO2017/046001
PCT Pub. Date: Mar. 23, 2017

(65) Prior Publication Data
US 2018/0251418 A1   Sep. 6, 2018

(30) Foreign Application Priority Data
Sep. 16, 2015   (EP) .................................... 15185441

(51) Int. Cl.
| | | |
|---|---|---|
| C07C 45/75 | (2006.01) | |
| C07C 67/39 | (2006.01) | |
| C07C 67/58 | (2006.01) | |
| C07C 51/09 | (2006.01) | |
| C07C 51/48 | (2006.01) | |
| C07C 47/22 | (2006.01) | |
| C07C 57/04 | (2006.01) | |
| C07C 67/54 | (2006.01) | |
| C07C 69/54 | (2006.01) | |

(52) U.S. Cl.
CPC .............. *C07C 67/39* (2013.01); *C07C 45/75* (2013.01); *C07C 47/22* (2013.01); *C07C 51/09* (2013.01); *C07C 51/48* (2013.01); *C07C 57/04* (2013.01); *C07C 67/54* (2013.01); *C07C 67/58* (2013.01); *C07C 69/54* (2013.01); *C07C 2527/03* (2013.01); *C07C 2527/054* (2013.01)

(58) Field of Classification Search
None
See application file for complete search history.

(56) References Cited

U.S. PATENT DOCUMENTS

| | | |
|---|---|---|
| 3,487,101 A | 12/1969 | Völker et al. |
| 4,496,770 A | 1/1985 | Duembgen et al. |
| 7,253,307 B1 | 8/2007 | Carlson, Jr. et al. |
| 8,791,296 B2 | 7/2014 | Broell et al. |
| 9,890,105 B2 | 2/2018 | Krill et al. |
| 2014/0051886 A1 | 2/2014 | Broell et al. |
| 2016/0068464 A1 | 3/2016 | Krill et al. |

FOREIGN PATENT DOCUMENTS

| | | |
|---|---|---|
| DE | 102011076642 A1 | 11/2012 |
| EP | 0 092 097 A1 | 10/1983 |
| EP | 0 487 853 B1 | 12/1995 |
| EP | 2 714 640 A1 | 4/2014 |
| WO | 2014/170223 A1 | 10/2014 |

OTHER PUBLICATIONS

International Search Report dated Nov. 11, 2016, in PCT/EP2016/071241, filed Sep. 9, 2016.
Weissermel, "Methacrylic Acid and its Esters" Industrial Organic Chemistry, VCH, Weinheim, 4 Edition, 1994, 8 Pages (submitting English translation only).
Kirk Othmer, "Methacrylic Acid and Derivatives" Encyclopedia of Chemical Technology $3^{rd}$ Edition, vol. 15, Feb. 28, 2018, pp. 346-350.

*Primary Examiner* — Ana Z Muresan
(74) *Attorney, Agent, or Firm* — Oblon, McClelland, Maier & Neustadt, L.L.P.

(57) ABSTRACT

The present invention relates to a process for preparing alkyl methacrylates, especially MMA, and methacrylic acid, based on methacrolein, which has been oxidatively esterified in a second process stage. Methacrolein is obtainable in principle from $C_2$ and $C_4$ units. The present process has the advantage that the alkyl methacrylate and methacrylic acid can be obtained in a simple manner, in high yields and high purities, either as a mixture or as isolated product streams. In particular, the process of the invention has the great advantage that especially the ratio of the desired methacrylic acid and alkyl methacrylate, especially MMA, products can be adjusted freely within a wide range and varied by chemical engineering measures and operating parameters.

17 Claims, 3 Drawing Sheets

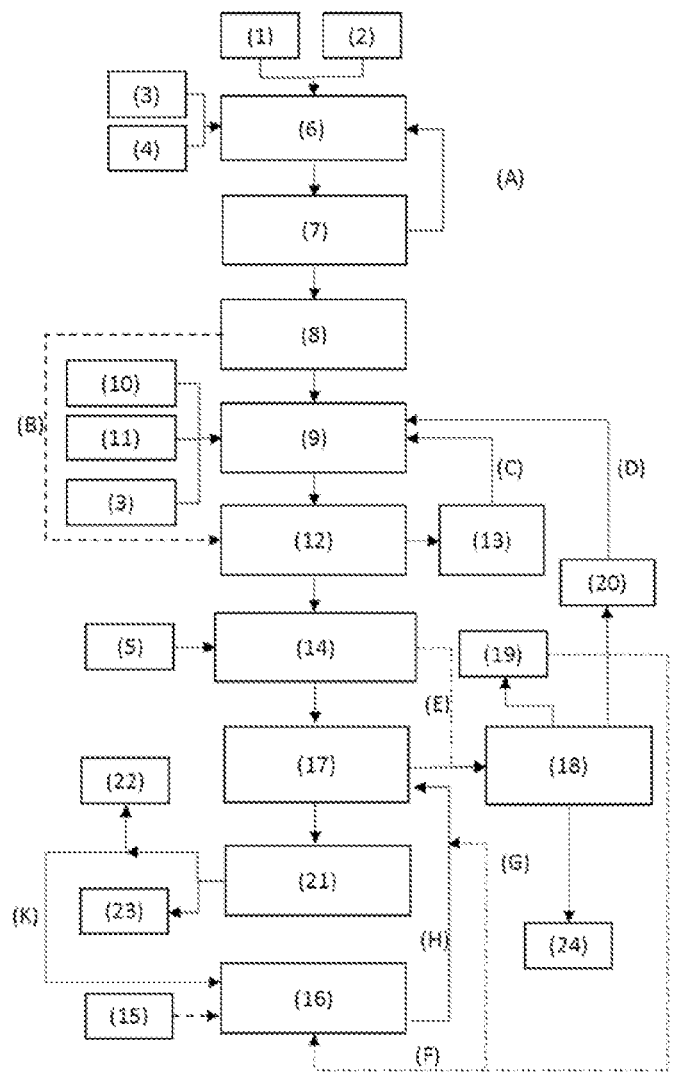

SYNTHESIS OF METHACRYLIC ACID FROM METHACROLEIN-BASED ALKYL METHACRYLATE

FIELD OF THE INVENTION

The present invention relates to a process for preparing alkyl methacrylates, especially MMA, and methacrylic acid, based on methacrolein, which is oxidatively esterified to give an alkyl methacrylate. Methacrolein is obtainable in principle from $C_2$ and $C_4$ units. The present process has the advantage that the alkyl methacrylate and methacrylic acid can be obtained in a simple manner, in high yields and high purities, either as a mixture or as isolated product streams. In particular, the process of the invention has the great advantage that especially the ratio of the desired methacrylic acid and alkyl methacrylate, especially MMA, products can be adjusted freely within a wide range and varied by chemical engineering measures and operating parameters.

PRIOR ART

The prior art discloses a multitude of processes for preparing methacrylic acid.

A standard procedure involves the controlled oxidation of hydrocarbon gases, for example butylene. Disadvantages of these processes are the comparatively low yields viewed overall that are obtained thereby.

In addition, methacrylic acid can be obtained by the reaction of methacrylamide with water. This process is more particularly described in U.S. Pat. No. 7,253,307. According to this publication, the reaction of methacrylamide with water can be effected in a stirred tank reactor or a tubular reactor. Preferably, the reaction is conducted at a pressure in the range from 3.65 to 7.70 bar and at a temperature in the range from 50 to 210° C.

The processes described in U.S. Pat. No. 7,253,307 for preparing methacrylic acid already lead to good yields combined with a high purity. However, methacrylic acid is an important product in the chemical industry which serves as a starting material for many important products. Therefore, a maximum yield and a particularly high purity combined with low production costs are essential for the economic success of such a preparation process. Even relatively small improvements in terms of the yields, the onstream times of the plants or similar process features lead to an important advance in terms of the waste volumes and production costs. Methacrylamide itself is typically prepared by the acetone cyanohydrin (ACH for short) sulpho process based on hydrogen cyanide and acetone in the presence of a great excess of sulphuric acid. The process generates large amounts of waste sulphuric acid and organically contaminated ammonium hydrogensulphate solution. These can be worked up only with great energy expenditure to give sulphuric acid. It is likewise possible for α-hydroxyisobutyric acid (HIBA) to serve as starting material for preparation of methacrylic acid. Such a process is described, for example, in U.S. Pat. No. 3,487,101, where the preparation of various methacrylic acid derivatives, especially methacrylic acid and methacrylic esters, proceeding from 2-hydroxyisobutyric acid (HIBA) in the liquid phase, is characterized in that the conversion of HIBA to methacrylic acid is conducted in the presence of a dissolved basic catalyst at high temperatures between 180-320° C. in the presence of high-boiling esters (e.g. dimethyl phthalate) and cyclic anhydrides (e.g. phthalic anhydride). According to the patent, at HIBA conversions of >90%, MAA selectivities around 98% are achieved. No statements are made as to the long-term stability of the liquid catalyst solution, especially the stability of the anhydride used, under the reaction conditions.

RU 89631 relates to a process for preparing methacrylic acid proceeding from HIBA by elimination of water in the liquid phase, characterized in that the reaction is conducted in the absence of a catalyst with an aqueous solution of HIBA (up to 62% by weight of HIBA in water) under pressure at high temperatures of 200° C.-240° C.

In addition, there has been intense study of the use of propene as base raw material, arriving at methacrylic acid in moderate yields via the stages of hydrocarbonylation to give isobutyric acid and dehydrogenating oxidation. This is a reaction of propene with carbon monoxide, hydrofluoric acid or concentrated sulphuric acid, and involves the subsequent hydrolysis of the intermediates in the presence of water. The process is not employed in production.

Another known method is to use propanal, which is obtainable in industrial processes proceeding from ethylene and C-1 units such as carbon monoxide, as base raw material. In these processes, the reaction is effected in an aldolizing reaction with formaldehyde, by dehydration of the β-hydroxycarbonyl compound formed in situ to give the corresponding α,β-unsaturated compound, methacrolein.

An overview of the standard processes for preparing methacrylic acid and esters thereof can be found in the literature, for example Weissermel, Arpe "Industrielle organische Chemie" [Industrial Organic Chemistry], VCH, Weinheim 1994, 4th edition, p. 305 if, or Kirk Othmer "Encyclopedia of Chemical Technology", 3rd edition, vol. 15, page 357.

EP 0 487 853 describes the preparation of methacrylic acid proceeding from acetone cyanohydrin (ACH), characterized in that, in the first step, ACH is reacted with water at moderate temperatures in the presence of a heterogeneous hydrolysis catalyst and, in the second step, α-hydroxyisobutyramide is reacted with methyl formate or methanol/carbon monoxide to form formamide and methyl hydroxyisobutyrate (MHIB), and, in the third step, MHIB is hydrolysed with water in the presence of a heterogeneous ion exchanger to give HIBA, and, in the fourth step, HIBA is dehydrated by allowing it to react in the liquid phase at high temperatures in the presence of a soluble alkali metal salt. Methacrylic acid preparation from HIBA is described at high conversions of around 99% with more or less quantitative selectivities. The multitude of reaction steps needed and the necessity of intermediately isolating individual intermediates, especially also the performance of individual operating steps at elevated pressure, make the process complicated and hence ultimately uneconomic. In addition, formamide is necessarily used, this compound being one which in many cases has to be considered as an undesired by-product which has to be disposed of in a costly manner. In a further variant, formamide can be used to prepare HCN. Ultimately, however, the disadvantages of the multistage reaction with costly and inconvenient circulation streams remain here, which in turn leads to a high energy expenditure and especially to a high specific steam consumption.

Finally, EP 2 714 640 discloses a process in which the methacrylic acid is obtained by hydrolysis of ACH-based methyl methacrylate (MMA). This involves first converting the ACH to methacrylamide and then esterifying the latter with methanol to give MMA. Thus, in this process for MMA preparation, in contrast to other processes, there is no way of discharging methacrylic acid in the form of an intermediate. In addition, the water supplied has to be heated. This is disadvantageous particularly from an energetic point of view because of the high heat capacity of water and the associated relevant energy input.

However, such a hydrolysis is known only for this specific ACH process. However, there are now more efficient alternatives for preparation of MMA which likewise do not have methacrylic acid as by-product. For instance, WO 2014/170223 describes a very efficient process in which propionaldehyde is obtained from $C_2$ fractions in a first stage and the latter is reacted in a second stage with formaldehyde to give methacrolein (MAL). This MAL in turn can then be oxidatively esterified in the presence of specific metal or metal oxide catalysts and of methanol to give MMA. Compared to all the other methods, this process features a particularly high yield and particularly good selectivities. However, it has the disadvantage that methacrylic acid is likewise obtained only to a very small degree, if at all, as by-product.

No application of the hydrolysis method known from EP 2 714 640 to this MMA preparation is known, especially since this hydrolysis method describes the use of purified MMA and not of intermediate mixtures comprising MMA alongside the by-products specifically generated in this process.

Another important factor in this connection is that, according to the technology and raw material basis used, other problematic by-products form in each case, and so it makes a great difference whether the MMA is produced from an ACH sulpho process or, for example, on the basis of a C-2 raw material (ethylene) as described in WO 2014/170223.

Simple integration of an MMA to methacrylic acid (MAA) hydrolysis as described in EP 2 714 640 into an MMA preparation process proceeding from methacrolein would mean that many additional separation steps would have to be incorporated, which would in turn cause high additional capital costs and would not have any synergistic effects overall between two processes.

Nor is this easy to implement, since the $C_2$-based MMA according to WO 2014/170223, especially in the workup steps, has an entirely different by-products spectrum which has to be taken into account with regard to high yields and selectivities. Thus, it is known that the MMA which has been prepared according to WO 2014/170223 can have a tendency to yellow colours in spite of purification. Furthermore, this crude MMA contains, in particular, relatively high concentrations of methacrylic acid, of 1,1-dimethoxyisobutene or of Michael products of MAL and dimeric MAL, and the conversion products thereof from the oxidative esterification, for example the corresponding acids and methyl esters. Particularly dimeric MAL thus leads to relevant amounts of methyl ester and/or acid in the MMA. If one wishes to avoid these unwanted by-products, it is necessary to purify the MMA prior to the hydrolysis. This is effected primarily by means of distillation. However, this removes the methacrylic acid likewise obtained as a by-product of the oxidative esterification and hence it is lost from the yield.

Finally, EP 0 092 097 discloses a C2-based process conducted via the methacrolein (MAL) intermediate. Here, methacrylic acid is produced directly in a gas phase step that follows the MAL synthesis and can optionally be discharged, worked up and isolated. The actual aim of the process is the esterification with methanol to give MMA in a third stage. Thus, this process is suitable for preparing methacrylic acid alongside MMA, but the achievable yields are limited by the unsatisfactory step from MAL to MAA in the gas phase, which has an overall adverse effect in the economic viability of the process. A particular disadvantage of this process, which is efficient in terms of the raw material basis, is the subsequent conversion in the gas phase over a heteropolyacid. In this case, only partial conversions of the MAL are achieved and the yield, even according to the patent literature, is not more than 80% to 85% of methacrylic acid. Even in the gas phase, the presence of by-products from the MAL preparation from propionaldehyde such as dimeric methacrolein and pentenals has adverse effects, and so these by-products have to be strictly limited.

Many of the processes detailed, especially for hydrolysis, additionally have the disadvantage that water has to be introduced into the system. However, the water has to be heated up to the reaction temperature prior to the addition or in the reactor.

In summary, it should be emphasized that there is no economically viable and technically obvious or technically simple solution to date in order to prepare MMA alongside methacrylic acid, for example based on methacrolein as starting basis and raw material, and at the same time in particular to prepare the product ratio of the two materials of value within a broad range with simultaneously good overall yields and ultimately with optimal economic viability.

Problem

The problem addressed by the invention is therefore that of providing a novel efficient and economically attractive process for preparing alkyl methacrylates, especially MMA, and simultaneously methacrylic acid proceeding from $C_2$ units.

More particularly, a process by means of which the problem of varying market requirements or market demands for methacrylic acid and MMA is taken into account and, for this purpose, the two products of value can be produced in a virtually freely selectable range via the selection of appropriate chemical engineering parameters is to be provided.

Furthermore, the novel process is to consume less energy, and enable higher overall yields of methacrylic acid or alkyl methacrylates, especially MMA.

In addition, the alkyl methacrylates and methacrylic acid prepared by means of the process are to have low colour numbers.

It was a particular problem addressed by the present invention to avoid the cited disadvantages of other processes; more particularly, the ratio of alkyl methacrylates and methacrylic acid in the product is to be controllable via the process regime and the operating parameters.

A further problem addressed was that of providing a process for preparing methacrylic acid by hydrolysis of MMA, in which no additional water has to be added to the system.

Further problems not stated explicitly may become apparent from the description or the claims.

Solution

These problems were solved by provision of a novel process for preparing methacrylic acid having the following operating steps:
a) synthesis of methacrolein in a reactor I,
b) oxidative esterification of methacrolein with an alcohol and oxygen to give an alkyl methacrylate in a reactor II and
e) reaction of at least a portion of the alkyl methacrylate with water to give methacrylic acid in a reactor III.

Especially preferred in accordance with the invention are processes having, in more detail, the following operating steps:

a) synthesis of methacrolein in a reactor I,
b) oxidative esterification of methacrolein with an alcohol and oxygen to give an alkyl methacrylate in a reactor II,
c) removal of the excess methacrolein and at least partial removal of the alcohol, followed by optional treatment with an acid and optional phase separation of the alkyl methacrylate-containing composition,
d) separation of the alkyl methacrylate- and optionally methacrylic acid-containing composition with supply of water as an organic phase from an aqueous phase in an extraction I,
e) reaction of at least a portion of the alkyl methacrylate with water to give methacrylic acid in a reactor III,
f) transfer of the composition comprising methacrylic acid and alkyl methacrylates from operating step e) into the extraction I from operating step d) and
g) optional separation of the methacrylic acid from the alkyl methacrylate in a separation stage M.

The process of the invention can be applied to all processes based on methacrolein and subsequent oxidative esterification of this methacrolein. The methacrolein may have been produced on a C2 or C4 basis. More particularly, the inventive process may be applied to the combinations of a C2-based process for preparing methacrolein and a subsequent oxidative esterification to give an alkyl methacrylate. This relates especially to the processes described in DE 3 213 681, U.S. Pat. No. 4,408,079, CN 1 038 461 04 and in the European patent application having application reference 14185345.7.

A particular aspect of the present invention is the possibility of being able to configure the water flows within the overall process in a particularly energy-saving manner and adjusting by-product formation in individual operating steps, in such a way that they do not disrupt one another. Thus, water is fed to the process in various stages. This relates firstly to stage a), in which water is supplied to reactor I (6), for example with formaldehyde (1), the base (3) and/or the acid (4). The exact water content in the methacrolein product output after isolation (8), which is relevant in terms of the formation of by-products, can be influenced depending on further process and isolation parameters such as temperature, pressure, catalyst concentration or residence time, and can be optimized by the person skilled in the art on the basis of the known prior art for this process stage. The methacrolein prepared with optimal process parameters, as described, for example, in the European patent application having reference number 14185345.7, is introduced directly or via (12) into the reactor II (9), where the water content rises merely as a result of the water that forms in the reaction. In addition, this may also be supplemented by further water content as a result of the base added and possibly the alcohol added. Particularly in this stage, the exact water content should be noted, since the formation of by-products here may depend very particularly thereon. Further addition of water may subsequently result from the preferred addition of an acid (14).

In an equally preferred variant of the present invention, the alcohol formed in operating step e) is wholly or partly removed and wholly or partly fed back to the reactor II for oxidative esterification in operating step b).

In that case, the removal of the water from the reaction mixture is first effected in operating step c), for example in an optional phase separation, and operating step d), the extraction I (17), together with the alcohol present. Preferably, this mixture is separated into alcohol (20) and water (19) in a further column (18). According to the pressure, this water still has a temperature of about 100° C. and can, firstly, be disposed of together with the column bottoms. Preferably, however—and here lies a further advantage of the invention—this water (19) is fed wholly or partly to the reactor III in operating stage e). This has the particular advantage that it does not have to be additionally heated like externally supplied water and hence the process can be conducted in a particularly economically viable manner and with the avoidance of large volumes of water for disposal. This recycling of the water supplied above from operating steps a) to b), and of the water of reaction from operating step b), can be implemented in all the embodiments described—as shown by way of example by the dotted lines (F) in FIGS. 1 to 3. Alternatively or additionally, it is also possible to direct (G) substreams of this water back into the extraction I (17). In addition, it is necessary to send at least a substream of the water removed (19) to a means of disposal, since water would otherwise accumulate within the overall operation, more specifically in components (16), (17) and (18). The person skilled in the art should adjust this substream such that the water content in these components, and hence in operating steps d), e) and f), irrespective of their sequence, remains constant.

The extraction I may optionally be preceded upstream by a further phase separation. The aqueous phase from this phase separation comprises proportions of the alcohol, water and the alkali metal salt of methacrylic acid and/or the alkali metal salt of the added mineral acid. For example, further treatment of this aqueous phase may correspond to that of the aqueous phase of the downstream extraction (17). The organic phase from the phase separation is transferred into the extraction I.

Therefore, irrespective of the embodiment of the present invention used, it is particularly preferable when water of reaction formed in operating step b) is separated from the alkyl methacrylate between operating steps b) and e), especially in operating step d), and fed wholly or partly back to the reactor III for hydrolysis in operating step e). Equally preferably, and in a supplementary measure or independently of the water streams, the removed alcohol from the hydrolysis in reactor III is fed back to the oxidative esterification in reactor II and hence likewise reused.

It has been found that, surprisingly, with the process of the invention, a methacrylic acid synthesis which is easily implementable on the industrial scale can be provided. The process is notable for the abovementioned advantages and for a small by-product spectrum. The isolated methacrylic acid obtained has a purity of usually greater than 99.5%.

Operating steps a) to c) are known to the person skilled in the art in general terms particularly on a C2 raw material basis and can be read about, for example, in WO 2014/170223 or the international patent application having filing reference PCT/EP 2014/068171. The methacrolein in operating step a) may be synthesized on the basis of $C_4$ units, such as isobutene or tert-butanol, or on the basis of $C_1$ and $C_2$ units, especially from propanal and formaldehyde, the propanal being obtained in turn from ethylene, hydrogen and carbon monoxide.

Preferably, the methacrolein is prepared in operating step a) from propionaldehyde and formaldehyde via a Mannich condensation. More preferably, the methacrolein removed in operating step c) and—at least in part—the excess alcohol are recycled into the reactor II.

For the process of the invention, it is very advantageous to minimize the by-product of a cyclic dimeric methacrolein formed in the methacrolein synthesis, or to remove this by-product from the reaction mixture prior to the hydrolysis. The dimeric methacrolein is esterified selectively in reactor II to give the alkyl ester of dimeric methacrolein and would thus get into the downstream stages. In the hydrolysis, this ester would in turn be hydrolysed to give the free acid of dimeric methacrolein. These by-products of dimeric methacrolein, the alkyl ester thereof and the corresponding free acid are effectively separated from the target products in the process of the invention by an appropriately configured product workup.

More particularly, there are three equally preferred embodiments of the present invention. These three variants differ particularly in the flow regime and hence partly also in the sequence of the individual operating steps. In all three embodiments, the operation is performable in an identical manner apart from an admixing operation with an acid (14) which preferably takes place in operating step c) and an optional phase separation.

More particularly, the operation up to this step proceeds from the synthesis of the methacrolein in reactor I (6) from formaldehyde (1), propionaldehyde (2), with addition of a catalyst formed from at least one base (3) and an acid (4). Preferably, the discharge of the reaction product is directly followed by a removal, for example a distillative removal, of the catalyst (7) and the recycling of this catalyst (A) into reactor I (6). The methacrolein-containing phase obtained is subsequently purified further, for example in a phase separation (8). The aqueous phase can be recycled to the distillation column (7). After the phase separation (8), further separation steps, for example an additional distillation column for further MAL purification, may optionally be installed. Subsequently, the purified methacrolein is introduced into reactor II (9) for oxidative esterification with supply of alcohol, especially methanol (10), of a base (3), which may be different from or identical to the base in reactor I, and of oxygen (11), which is optionally fed in as air, pure gas or preferably as a mixture with nitrogen. The output from reactor II (9) is subsequently purified in such a way that excess methacrolein is isolated, preferably as a mixture (13), for example with alcohol, and is recycled (C) back into reactor II (9). This can be effected, for example, in a distillation column (12). In one variant of this process, the methacrolein is optionally directed wholly or partly from the operating stage (8) directly into the distillation (12), in order to be directed thence via (C) into reactor II (9).

The first embodiment is shown by way of example in FIG. 1. In this variant, the product stream from operating step c) which comprises an alkyl methacrylate, after the optional admixing with an acid and optional phase separation (14), is directed directly into reactor III (16) for performance of operating step e). Water is additionally fed into reactor III, which can be effected in the form of fresh water (15) and/or from an appropriate recycling stream (F). In operating step f), the transfer (H) (corresponding to operating step f) of the product from reactor III (16) into the extraction I (17) for performance of operating step d) is then effected. The first phase from this extraction, comprising the alkyl methacrylate, especially MMA, and the methacrylic acid is directed into the separation stage M for further separation. This corresponds to operating step g), from which an alkyl methacrylate, especially MMA stream (22), and a methacrylic acid-containing stream (23) are obtained. These can each be subjected to further purification stages. Especially in the case of the methacrylic acid-containing stream, it can also be used directly in the presence of relevant residual amounts of the alkyl methacrylate. It is also possible to isolate a mixed stream of the two products prior to the extraction, in order to purify them together and send them to a use as a mixture. The predominantly aqueous phase from the extraction I (17), comprising the alcohol which has been released in the hydrolysis, is sent to a further, preferably distillative, separation (18). In this separation, a bottoms phase is isolated for disposal or for further processing (24). The water phase (19) is either disposed of or guided into reactor III (16) (conduit (F)) and/or into the extraction I (17) (conduit (G)). The isolated alcohol (20), especially the isolated methanol in the case of an MMA synthesis, optionally together with small amounts of other substances, for example MMA, water, etc., is guided into reactor II (conduit D)).

In summary, this embodiment is effected in such a way that, after operating step e), the further operating steps are conducted in the sequence f), d) and g).

In the second, likewise preferred embodiment, the alkyl methacrylate-containing composition from operating step c), for performance of operating step d), contrary to the first embodiment, is directed not directly into the reactor III (16) but into the extraction I (17). Subsequently, the organic phase from operating step d), and hence from the extraction I (17), is fed in one substream to the reactor III (16) for performance of operating step e) (conduit (J)) and in another substream to the separation stage M (21) for performance of operating step g) (conduit (I)). Otherwise, the overall process is constructed analogously to the first embodiment. One advantage of this embodiment is that it is possible by means of connection of the streams (I) and (J) to flexibly control the proportion of alkyl methacrylate produced and methacrylic acid produced in each case. The formation of the methacrylic acid by hydrolysis or saponification from an alkyl methacrylate is an equilibrium reaction. The equilibrium or conversion is controlled via the process parameters, for example temperature, reactant or product concentrations in reactor III. If the product mixture of this reaction is then recycled from the reactor III (16) back into the extraction I (17) (this stream also exists in embodiment 1), the alcohol released (for example methanol) is removed from the system therein. The now reduced-alcohol mixture, in this embodiment, is subsequently directed back into reactor III, where further acid formation can be effected by means of the reaction, the equilibrium of which has now been moved. Thus, an increase in methacrylic acid formation in particular compared to embodiment 1 is possible by this embodiment. An illustrative, schematic view of this embodiment can be found in FIG. 2. In summary, this embodiment is effected in such a way that, after operating step c), the further operating steps are conducted in the sequence d), e), f) and g), this mode of connection resulting in a circulation regime of operating steps d), e) and f).

In the third, likewise preferred embodiment, as shown by way of example in FIG. 3, the alkyl methacrylate-containing composition from operating step c) is directed into the extraction I (17) for performance of operating step d). Subsequently, the organic phase from operating step d) is directed into the separation stage M (21) for performance of operating step g), in which case a substream (K) from the separation stage M (21) is subsequently fed to the reactor III (16) for performance of operating step e). In this case, the substream (K) is withdrawn especially from the alkyl methacrylate phase of the separation stage M (21). The hydrolysis product from reactor III (16), finally, as in the two other embodiments, is transferred via the conduit (H) back into the extraction I (17). In summary, the reaction here is accordingly effected, after operating step c), in the sequence d), g), e) and f), these four latter component steps being operated at least partly and/or temporarily in a circulation regime.

Optionally, operating step c) or operating step d), irrespective of the embodiment used, may be followed by a further distillation before the alkyl methacrylate-containing phase in operating step e) is directed into reactor III. By means of this distillation, the alkyl methacrylate-containing phase is freed of high-boiling constituents. For this purpose, the alkyl methacrylate-containing phase is introduced into the lower half of a distillation column in a manner known to the person skilled in the art. The distillation column may in principle correspond to any design that appears suitable to the person skilled in the art.

It is preferably and generally the case that the alcohol in operating step b) is methanol and the alkyl methacrylate is methyl methacrylate. However, it is also quite possible to conduct this reaction with all alcohols known for synthesis of alkyl methacrylates, or di-, tri- or tetramethacrylates. Other examples of such alcohols are accordingly ethanol, propanol, n-, iso- or tert-butanol, 2-ethylhexanol or octanol. One example for dimethacrylates is glycol. It is likewise possible to use functional alcohols here, for example 2-hydroxyethyldimethylamine or monothioglycol.

In a particular embodiment, the aqueous phase from operating step d) is separated into water, an alcohol and a waste stream, the water being fed wholly or partly into reactor III, the alcohol wholly or partly into reactor II, and the waste stream to a disposal.

With regard to operating step e), various catalysts are suitable for hydrolysis. As a result of the use of heterogeneous catalysts, there is no need to subsequently remove the catalyst residues from the methacrylic acid prepared. Especially suitable for the inventive hydrolysis by means of heterogeneous catalysts in operating step d) are zeolites, ion exchange resins and amorphous acid catalysts. It is also possible to use mixtures of different catalysts. It has been found that cationic ion exchange resins are particularly preferred. Examples of suitable catalysts are ion exchangers such as Lewatit K1221, from Lanxess AG, Lewatit K2629, from Lanxess AG, Dowex CM-4, from Dow Chemical, Dowex M-31, from Dow Chemical, Dowex M-3 MS, from Dow Chemical, Amberlyst 39 Wet, from Rohm & Haas, Amberlyst CSP2, from Rohm & Haas, Amberlyst CSP3, from Rohm & Haas, DIAION PK208, from Mitsubishi Chemicals, DIAION PK216, from Mitsubishi Chemicals, DIAION PK228, from Mitsubishi Chemicals.

For the individual catalysts, there are also respective preferred configurations of the reactor III, which may quite possibly differ from one another. For example, for zeolites or amorphous acid catalysts, it is especially possible to use a catalyst bed in reactor III. Particular preference is given here to flow through the reactor III from the top.

Such a reactor can also be used for ion exchange resins. An alternative would be to use a circulation reactor. In this case, the alkyl methacrylate phase is conducted, optionally repeatedly, through the circuit. This is controlled, for example, by virtue of the withdrawal rate from the reactor being much less than the circulation rate in the reactor. The mass or volume ratio of the circulation stream to the feed stream by means of which the alkyl methacrylate-containing phase is directed into the reactor III is preferably 5 to 50, more preferably 15 to 30.

Especially in the case of cationic exchange resins, it has additionally been found to be advantageous here when the alkyl methacrylate phase is admixed with an acid, preferably with sulphuric acid, prior to or on addition to the reactor III. Even small amounts are sufficient here, for example of 0.01 to 2 mol %, based on the alkyl methacrylate.

Because of the base added in reactor II, for example NaOH, methacrylic acid obtained as a by-product is converted in this case to the corresponding methacrylate salt, for example sodium methacrylate. The addition of acid (14) converts these salts back to free methacrylic acid. In the oxidative esterification, according to the process regime, up to 5% by weight, generally around 3% by weight, of methacrylic acid is obtained as a by-product. If this acid is directed to a cationic ion exchanger in salt form, the metal ion would remain thereon, there would be a loss of effectiveness, and subsequent regeneration of the ion exchanger would be necessary. The addition of the strong acid dispenses with any such consumption. Furthermore, the presence of small amounts of this acid, especially sulphuric acid, results in simultaneous regeneration of the ion exchange resin in operation.

It has been found to be particularly advantageous to conduct the hydrolysis at a temperature of 50 to 200° C., preferably of 90 to 120° C. and especially between 100 and 110° C. It has likewise been found to be advantageous to conduct the reaction at a pressure of 1.1 to 10 bar, preferably of 1.5 to 6 bar. The manner of pressure adjustment in the reactor is by measurement of this pressure at the reactor outlet.

Alternatively, the reaction in operating step e) in reactor III can be effected entirely in the presence of homogeneous catalysts selected from the group of the mineral and/or organic acids, preferably sulphuric acid, methanesulphonic acid or toluenesulphonic acid, at a temperature of 50 to 200° C., preferably of 90 to 170° C., and at a pressure of 1.1 to 10 bar, preferably of 1.5 to 6 bar.

The residence time in reactor III depends especially on the reactor volume and on the flow rates within the reactor.

Reactant concentrations, conversion and temperature in reactor III can be adjusted such that the reaction mixture in the reactor always remains monophasic. However, a hydrolysis reaction in a biphasic organic-aqueous mixture is also possible.

The molar alkyl methacrylate/$H_2O$ ratio of the reactant stream in reactor III is preferably between 0.5 and 5, more preferably between 1.5 and 3. It is quite possible here to additionally pass small amounts of water into the reactor III. Preferably, however, operating step d) is conducted with the amount of water which is guided into reactor III in the aqueous alkyl methacrylate phase from operating step c). This water forms previously in operating step b) and thus there is preferably no need for external water supply, which has an overall positive effect on the economic viability of the process, especially from an energy point of view, since heating of the water phase is dispensed with.

The separation stage M in operating step g) is preferably at least one distillation, possibly also two or more distillations connected in series.

In one variant of the process of the invention, which can be used to obtain alkyl methacrylates and methacrylic acid in the respective amounts required, the introduction of the respective stream into the reactor III is preceded either by withdrawal of a substream for transfer into a workup or at least temporary diversion of the entire stream into the workup upstream of reactor III, in order to obtain pure alkyl methacrylate from this substream.

In principle, crude methacrylic acid or a crude alkyl methacrylate can be subjected to a further purification, in order to arrive at a very substantially pure product. This alternative operating step for purification may, for example, have one stage and especially be in the form of a multistage distillation or a crystallization. However, it has been found to be advantageous in many cases when such a purification comprises at least two or three stages. It is advisable for a prepurification by removal of the high-boiling constituents to be followed by a subsequent removal of the low-boiling constituents, followed by a main purification.

For purification of the methacrylic acid, the crude methacrylic acid can first be separated from low-boiling constituents by means of distillation. The methacrylic acid enriched in the column bottoms can be removed as crude methacrylic acid. Preferably, this crude methacrylic acid is separated from the high boilers present, for example stabilizers or by-products, in a further downstream vacuum rectification column and obtained as pure methacrylic acid via the top of the column or in a sidestream. The methacrylic acid thus obtained has a purity of ≥99.5%.

Alternatively, the methacrylic acid can also be purified by means of crystallization, which tends to give even higher purities. It is also possible to combine a distillation stage and a crystallization stage with one another.

Because of the polymerizability, it is preferable that one or more polymerization inhibitors are added to the process. This relates especially to all process stages of the overall process. Polymerization inhibitors, for example hydroquinones, hydroquinone ethers such as hydroquinone monomethyl ether or di-tert-butylcatechol, phenothiazine, N,N'-(diphenyl)-p-phenylenediamine, 4-hydroxy-2,2,6,6-tetramethylpiperidine 1-oxyl, p-phenylenediamine, methylene blue or sterically hindered phenols, are widely known in the specialist field. These compounds can be used individually or in the form of mixtures and are generally commercially available. The mode of action of the stabilizers is usually that they act as free-radical scavengers for the free radicals that occur in the polymerization. For further details, reference is made to the standard specialist literature, especially to the Römpp-Lexikon Chemie [Römpp's Chemistry Lexicon]; editors: J. Falbe, M. Regitz; Stuttgart, N.Y.; 10th edition (1996); under the heading "Antioxidantien" [Antioxidants] and the references cited there.

The process of the invention is operated in such a way that the molar proportion of methacrylic acid isolated in the sum total of methacrylic acid isolated and alkyl methacrylate isolated is between 0.02 and 1. Preferably, the process of the invention is operated in such a way that this ratio is between 0.05 and 0.5 and more preferably between 0.1 and 0.3. The methacrylic acid is formed in the process of the invention in operating steps b) and especially e). While methacrylic acid formation is comparatively low in operating step b) as a by-product, the formation of methacrylic acid in operating step e) can be controlled within a wide range by varying influencing factors such as the configuration of operating step e), especially in relation to the number of passes through operating steps d) and e), the control of the ratios of the product streams, withdrawing the alkyl methacrylate and directing it into the reactor III, and the composition in reactor III. In the simplest case, it is possible, for example, by increasing the water content in reactor III to control the formation of methacrylic acid, for example by influencing the equilibrium and the reaction rate. Because of the equilibrium reaction, a particularly high proportion of methacrylic acid to be formed of more than 50 mol % is comparatively disadvantageous in terms of energy.

As well as the process of the invention, a constituent of the present invention is a plant usable for the purpose of preparing alkyl methacrylates and methacrylic acid. Such a plant can especially be characterized in that it has at least the following apparatuses:

a) a reactor I for synthesis of methacrolein,
b) a reactor II for oxidative esterification of methacrolein to give an alkyl methacrylate in the presence of an alcohol and oxygen,
c) a first distillation column for distillation of the reactor output from reactor II, an optional treatment with an acid and optionally subsequent phase separation of the alkyl methacrylate-containing phase from the distillation,
d) an extraction I for separation of alkyl methacrylate- and optionally methacrylic acid-containing composition with supply of water into an organic phase and an aqueous phase,
e) a reactor III for partial hydrolysis of the alkyl methacrylate to methacrylic acid,
f) a pipeline from reactor III which leads directly or indirectly into the extraction I and
g) at least one second distillation column and/or an extraction for separation of the alkyl methacrylate from the methacrylic acid.

EXAMPLES

Example 1

The total energy consumption of the process for preparing MMA from methacrolein (according to FIG. 1, but without reactor III) was determined and compared with the corresponding values for a process of the invention for preparing MMA and MAA according to FIG. 1 to FIG. 3:

TABLE 1

| Example | Process | MMA [kt/a] | MAA [kt/a] | MMA eq. [kt/a] | Energy consumption [t steam/ t MMA eq.] |
| --- | --- | --- | --- | --- | --- |
| Comparative Example | (without rct. III) | 143 | 3 | 146 | 5.13 |
| Example 1 | as per FIG. 1 | 126 | 18 | 144 | 4.97 |
| Example 2 | as per FIG. 2 | 98 | 43 | 141 | 4.90 |
| Example 3 | as per FIG. 3 | 99 | 43 | 142 | 6.00 |

As apparent from Table 1, it is possible in all the inventive working examples to produce relatively high amounts of MAA in addition to MMA. The total energy requirement remains similar to the process without MAA production.

LIST OF REFERENCE NUMERALS

FIG. 3 shows a process regime according to embodiment 3. Here, the reaction is effected, after operating step c), in the sequence d), g), e) and f), these operating steps d), g), e) and f) being operated at least partly and/or temporarily in a circulation regime.

Figure 1:
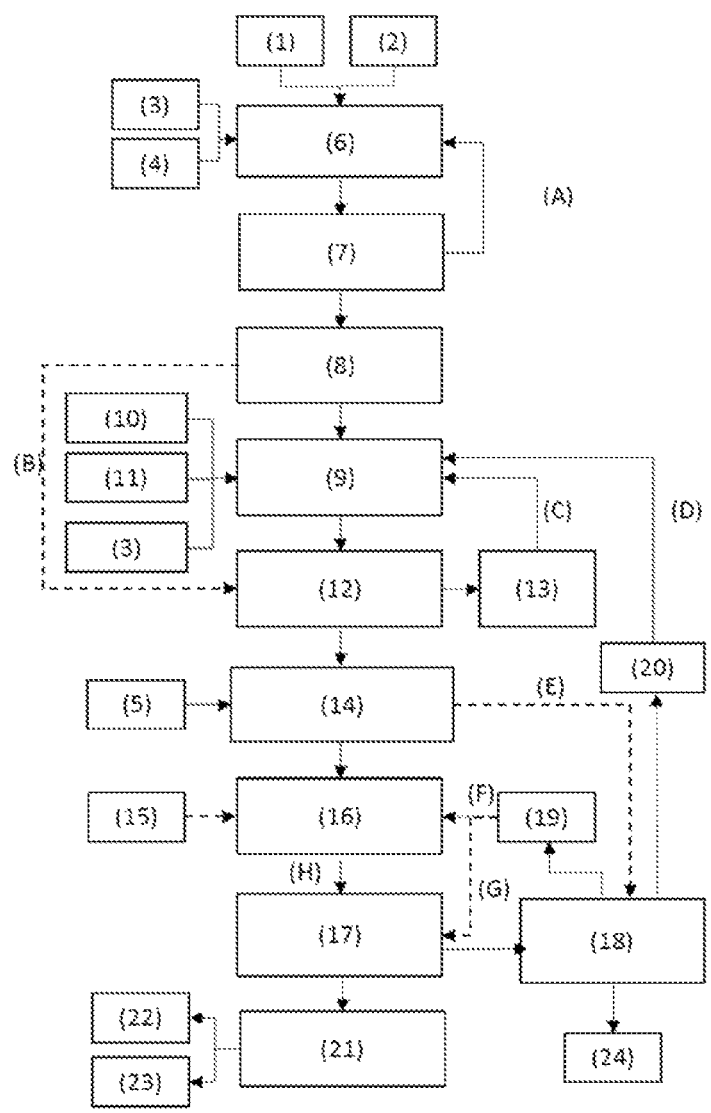
FIG. 1 shows a process regime according to embodiment 1. This embodiment is configured such that, after operating step e), the further operating steps are conducted in the sequence f), d) and g).
Figure 2:
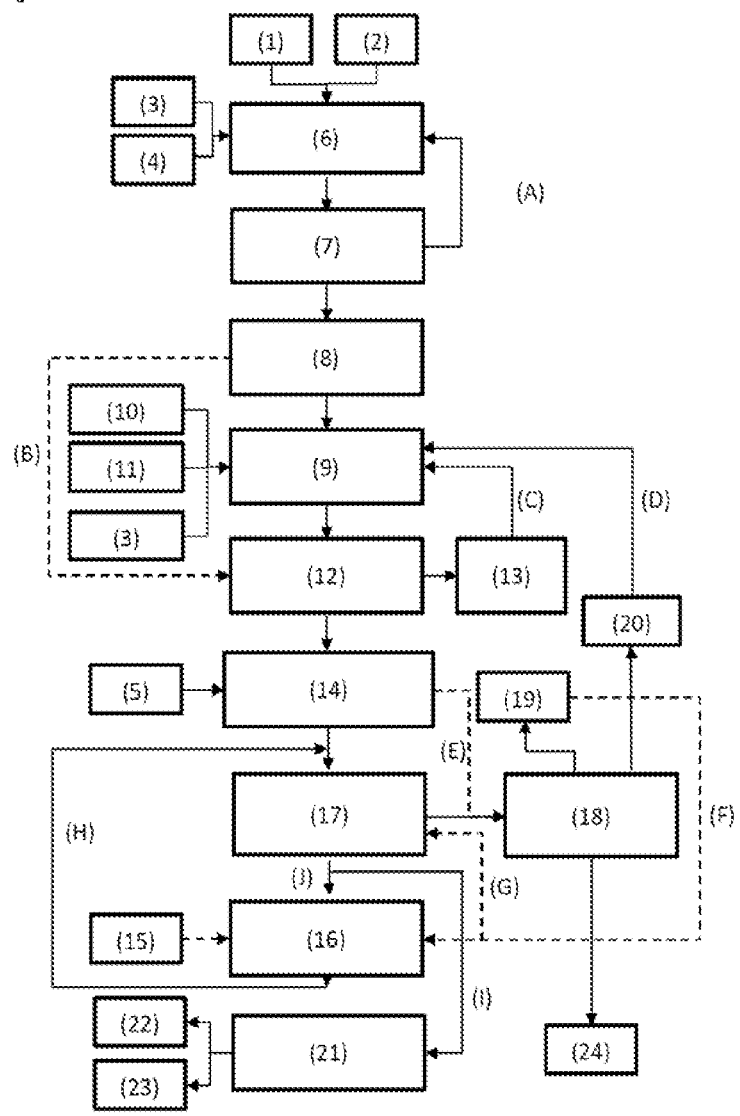
FIG. 2 shows a process regime according to embodiment 2. This embodiment is configured such that, after operating step c), the further operating steps are conducted in the sequence d), e), f) and g), this mode of connection resulting in a circulation regime of operating steps d), e) and f).

(1) Formaldehyde feed
(2) Propionaldehyde feed
(3) Inlet for a base
(4) Inlet for an acid I
(5) Inlet for an acid (II)
(6) Reactor I (synthesis of methacrolein; operating step a)
(7) Catalyst removal
(8) Isolation of methacrolein
(9) Reactor II (oxidative esterification; operating step b)
(10) Alcohol feed (e.g. methanol)
(11) Oxygen or air inlet
(12) Removal of methacrolein and alcohol (e.g. methanol) (operating step c)
(13) Isolated methacrolein/alcohol mixture
(14) Admixing with acid and optional phase separation
(15) Optional water and acid (II) addition
(16) Reactor III (hydrolysis to methacrylic acid; operating step e)
(17) Extraction I (operating step d)
(18) Separation of the isolated alcohol/$H_2O$ mixture (from operating step d)
(19) Removed $H_2O$ (for recycling or disposal)
(20) Isolated alcohol (e.g. methanol)
(21) Separation stage M (separation of alkyl methacrylate and methacrylic acid; operating step g)
(22) Isolated alkyl methacrylate for further purification
(23) Isolated methacrylic acid for further purification
(24) Disposal
Special conduits:
(A) Catalyst recycling into reactor I
(B) Optional transfer of the methacrolein stream into the methacrolein purification (12)
(C) Recycling of methacrolein removed (with methanol) into (9)
(D) Recycling of methanol into (9)
(E) Optional transfer of the aqueous phase from (14) into (18)
(F) Optional transfer of the water from (18) into (16)
(G) Optional transfer of the water from (18) into (17)
(H) Transfer of product stream from (16) into (17) (operating step f)
In FIG. 2 only:
(I) Substream from (17) into (21)
(J) Substream from (17) into (16)
In FIG. 3 only:
(K) Substream of the alkyl methacrylate phase (22) from (21) into (16)

The invention claimed is:

1. A process for preparing at least one alkyl methacrylate and methacrylic acid, the process comprising in the following order:
a) synthesizing methacrolein in a reactor I,
b) carrying out oxidative esterification of the methacrolein with an alcohol and oxygen to give an alkyl methacrylate in a reactor II and
e) reacting at least a portion of the alkyl methacrylate with water to give methacrylic acid in a reactor III.

2. The process according to claim 1, further comprising:
c) removing excess methacrolein and at least partially removing the alcohol, optionally followed by treating with an acid and/or by carrying out phase separation of an alkyl methacrylate-containing composition,
d) separating the alkyl methacrylate-containing composition and optionally a methacrylic acid-containing composition with supply of water as an organic phase from an aqueous phase in an extraction I,
f) transferring a composition comprising the methacrylic acid and the alkyl methacrylate from e) into the extraction I and
g) optionally separating the methacrylic acid from the alkyl methacrylate in a separation stage M.

3. The process according to claim 1,
wherein water of reaction formed in b) is separated from the alkyl methacrylate between b) and e) and fed wholly or partly back to the reactor III for hydrolysis in e).

4. The process according to claim 1,
wherein an alcohol formed in e) is wholly or partly removed and wholly or partly fed back to the reactor II for oxidative esterification in b).

5. The process according to claim 2,
wherein the alkyl methacrylate-containing composition from c) is passed into the reactor III for performance of e) and, after e), f), d) and g) are conducted in succession.

6. The process according to claim 2,
wherein the alkyl methacrylate-containing composition from c) is passed into the extraction I for performance of d), and
the organic phase from d) is then fed in a substream to the reactor III for performance of e) and in another substream to the separation stage M for performance of g).

7. The process according to claim 2,
wherein the alkyl methacrylate-containing composition from c) is passed into the extraction I for performance of d), and
the organic phase from d) is then guided into the separation stage M for performance of g), in which case a substream of an alkyl methacrylate phase from the separation stage M is then fed to the reactor III for performance of e).

8. The process according to claim 5,
wherein the aqueous phase from d) is separated into water, an alcohol and a waste stream, the water being fed wholly or partly into the reactor III, the alcohol wholly or partly into the reactor II, and the waste stream to a disposal.

9. The process according to claim 2,
wherein the methacrolein is prepared in a) from propionaldehyde and formaldehyde via a Mannich condensation, and
the methacrolein removed in c) and the alcohol are recycled into the reactor II.

10. The process according to claim 2,
wherein the separation stage M in g) is at least one distillation.

11. The process according to claim 1,
wherein the reacting in e) in the reactor III is effected in the presence of at least one heterogeneous catalyst selected from the group consisting of a zeolite, an ion exchange resin and an amorphous acid catalyst, at a temperature of 50 to 200° C. and at a pressure of 1.1 to 10 bar.

12. The process according to claim 1,
wherein the reacting in e) in the reactor III is effected in the presence of at least one homogeneous catalyst selected from the group consisting of a mineral, and an organic acid at a temperature of 50 to 200° C. and at a pressure of 1.1 to 10 bar.

13. The process according to claim 1,
wherein the alcohol is methanol and
the alkyl methacrylate is methyl methacrylate.

14. The process according to claim 1,
wherein an introduction of a respective stream into the reactor III to obtain pure alkyl methacrylate is preceded either by withdrawal of a substream for transfer into a workup or diversion of an entire stream at least temporarily upstream of the reactor III into the workup.

15. The process according to claim 1,
wherein the process is operated in such a way that a molar proportion of isolated methacrylic acid in a sum total of isolated methacrylic acid and isolated alkyl methacrylate is between 0.02 and 1.

16. The process according to claim 11,
wherein the at least one heterogeneous catalyst is a cationic ion exchange resin.

17. The process according to claim 12,
wherein the at least one heterogeneous catalyst is sulphuric acid, methanesulphonic acid or toluenesulphonic acid.

\* \* \* \* \*